US012582639B2

(12) United States Patent
Sim et al.

(10) Patent No.: US 12,582,639 B2
(45) Date of Patent: Mar. 24, 2026

(54) PREVENTIVE, RELIEF OR THERAPEUTIC USE OF 2,3,5-SUBSTITUTED THIOPHENE COMPOUND AGAINST GASTROINTESTINAL STROMAL TUMOR

(71) Applicants: PHAROS IBIO CO., LTD, Anyang-si (KR); KOREA INSTITUTE OF SCIENCE AND TECHNOLOGY, Seoul (KR)

(72) Inventors: Tae Bo Sim, Seoul (KR); Seung Hye Choi, Seoul (KR); Han Na Cho, Seoul (KR); Nam Kyoung Kim, Seoul (KR); Woo Young Hur, Seoul (KR); Chi Man Song, Seoul (KR); Ky Youb Nam, Goyang-si (KR); Jeong Hyeok Yoon, Yongin-si (KR)

(73) Assignees: PHAROS IBIO CO., LTD., Gyeonggi-Do (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 510 days.

(21) Appl. No.: 18/006,582

(22) PCT Filed: Jul. 30, 2021

(86) PCT No.: PCT/KR2021/009987
§ 371 (c)(1),
(2) Date: Jan. 24, 2023

(87) PCT Pub. No.: WO2022/025709
PCT Pub. Date: Feb. 3, 2022

(65) Prior Publication Data

US 2023/0270733 A1 Aug. 31, 2023

(30) Foreign Application Priority Data

Jul. 31, 2020 (KR) ........................ 10-2020-0095987

(51) Int. Cl.
*A61K 31/4535* (2006.01)
*A23L 33/10* (2016.01)
*A61P 35/00* (2006.01)

(52) U.S. Cl.
CPC .......... *A61K 31/4535* (2013.01); *A23L 33/10* (2016.08); *A61P 35/00* (2018.01)

(58) Field of Classification Search
None
See application file for complete search history.

(56) References Cited

U.S. PATENT DOCUMENTS

2019/0047993 A1* 2/2019 Sim ..................... A61K 31/381

FOREIGN PATENT DOCUMENTS

JP 2019504900 2/2019
KR 10-2006-0127127 A 12/2006

(Continued)

OTHER PUBLICATIONS

Demetri et al. NCCN Task Force Report: Management of Patients with Gastrointestinal Stromal Tumor (GIST)—Update of the NCCN Clinical Practice Guidelines. Journal of the National Comprehensive Cancer Network, vol. 5, Supplement 2: S1-S32 (2007). (Year: 2007).*

(Continued)

*Primary Examiner* — Jeffrey S Lundgren
*Assistant Examiner* — Sara Elizabeth Townsley
(74) *Attorney, Agent, or Firm* — Wenderoth, Lind & Ponack, L.L.P.

(57) ABSTRACT

The present invention relates to the use of a 2,3,5-substituted thiophene compound for the prevention, amelioration or treatment of gastrointestinal stromal tumor. The 2,3,5-substituted thiophene compound exhibits high inhibitory activity against the growth of gastrointestinal stromal tumor, and (Continued)

| Treatment Group | Median Survival (day) |
|---|---|
| Vehicle | 16 |
| Imatinib 90 mpk | 15 |
| Sunitinib 20 mpk | 16 |
| Sunitinib 40 mpk | 14 |
| PHI-101 7 mpk | 19 |
| PHI-101 20 mpk | 26 |
| PHI-101 40 mpk | 28 |
| PHI-101 80 mpk | 32 |

thus may be effectively used for the prevention, amelioration or treatment of gastrointestinal stromal tumor.

2 Claims, 8 Drawing Sheets

(56) References Cited

FOREIGN PATENT DOCUMENTS

| | | | |
|---|---|---|---|
| KR | 10-0885129 | B1 | 2/2009 |
| KR | 10-2015-0053894 | A | 5/2015 |
| KR | 10-2017-0096599 | | 8/2017 |
| KR | 10-2019-0091537 | | 8/2019 |

OTHER PUBLICATIONS

Corless, C.L. Gastrointestinal Stromal Tumors: what do we know now? Modern Pathology (2014) 27, S1-S16. (Year: 2014).*
International Search Report corresponding to PCT/KR2021/009987 mailed Dec. 3, 2021 (12 pages, including English translation).
Babaei, Maryam Abbaspour, et al., "Receptor tyrosine kinase (c-Kit) inhibitors: a potential therapeutic target in cancer cells", Drug Design, Development and Therapy. 10: 2443-2459 (2016).
Gardino, Alexandra K., et al., "Targeting kinases with precision", Molecular & Cellular Oncology. 5(3): e1435183 (2018).
Japanese Office Action corresponding to JP Application No. 2023-504835; mailed Dec. 11, 2023 (10 pages, including English translation).
Brems, Hilde, et al., "Mechanisms in the pathogenesis of malignant tumors in neurofibromatosis type 1", Lancet Oncol 10: 508-515, 2009.
Demetri, George D., et al., "NCCN Task Force Report: Optimal Management of Patients with Gastrointestinal Stromal Tumor (GIST)—Update of the NCCN Clinical Practice Guidelines", Journal of the National Comprehensive Cancer Network, vol. 5 Supplement 2: S1-S32, 2007.
Kaitsiotou, Helena, et al., "Inhibitors to Overcome Secondary Mutations in the Stem Cell Factor Receptor KIT", J. Medical. Chemistry 60: 8801-8815, 2017.
Krause, Daniela S., et al., "Tyrosine Kinases as Targets for Cancer Therapy", The New England Journal of Medicine 353: 172-187, 2005.
Wilhelm, Scott M., et al., "Regorafenib (BAY 73-4506): a new oral multikinase inhibitor of angiogenic, stromal and oncogenic receptor tyrosine kinases with potent preclinical antitumor activity", Int. J. Cancer 129: 245-255, 2011.

* cited by examiner

| Treatment Group | Median Survival (day) |
|---|---|
| Vehicle | 16 |
| Imatinib 90 mpk | 15 |
| Sunitinib 20 mpk | 16 |
| Sunitinib 40 mpk | 14 |
| PHI-101 7 mpk | 19 |
| PHI-101 20 mpk | 26 |
| PHI-101 40 mpk | 28 |
| PHI-101 80 mpk | 32 |

PREVENTIVE, RELIEF OR THERAPEUTIC USE OF 2,3,5-SUBSTITUTED THIOPHENE COMPOUND AGAINST GASTROINTESTINAL STROMAL TUMOR

TECHNICAL FIELD

The present invention relates to the use of a 2,3,5-substituted thiophene compound for the prevention, amelioration or treatment of gastrointestinal stromal tumor.

BACKGROUND ART

Gastrointestinal stromal tumor (GIST) is the most common sarcoma occurring in the gastrointestinal tract, mesentery or reticulum and accounts for 5% of all sarcomas. In general, only complete resection can achieve a cure for gastrointestinal stromal tumor, but recurrence in the liver or peritoneum is common even after surgery, and if resection is impossible or recurrence occurs, the gastrointestinal stromal tumor does not respond to palliative cytotoxic chemotherapy and radiotherapy, and thus the prognosis thereof is very poor. A specific cell signaling pathway involved in the development of gastrointestinal stromal tumor was revealed, and a phenomenal effect could be achieved by using imatinib (also called Glivec, Novartis) which is a targeted anticancer agent capable of blocking the cell signaling pathway. Since Glivec exhibits very mild side effects compared to previous cytotoxic anticancer agents, it has excellent effects not only on the prolongation of survival time but also on the quality of life. Based on these results, beyond the use of Glivec as a primary treatment for metastatic tumors, studies on the effects of Glivec as a preoperative treatment before surgery and as an adjuvant treatment after surgery have been conducted.

Gastrointestinal stromal tumor originates from Cajal stromal cells or their progenitor cells, and is a gastrointestinal tract mesenchymal tumor induced by KIT mutations (D816 and N822K). In most cases (90 to 95%), gastrointestinal stromal tumor is positive for c-kit protein and has a histological finding corresponding to a characteristic fusiform shape, an epithelioid shape, or a mixed shape thereof (Corless C L, Fletcher J A, Heinrich M C. Biology of gastro-intestinal stromal tumors. J Clin Oncol 2004; 22:3813-3825). Mutations in the KIT or PDGFRα gene are found in 85 to 90% of gastrointestinal stromal tumors, of which mutations in the KIT gene are the most common with a frequency of 75 to 80%. In particular, mutations in exon 11 account for about 70% of mutations in the KIT gene, mutations in exon 9 account for about 15%, and mutations in exons 13 and 17 are rare (less than 5%). Mutations in the PDGFRα gene are found in about ⅓ (about 7%) of gastrointestinal stromal tumors without KIT mutations (Yarden Y, Kuang W J, Yang-Feng T, et al. Human proto-oncogene c-kit: a new cell surface receptor tyrosine kinase for an unidentified ligand. EMBO J 1987; 6:3341-3351). In gastrointestinal stromal tumors, KIT receptor protein is self-activated by KIT gene mutations (D816 and N822K) even in the absence of ligand stimulation, and cell division is continuously promoted, causing tumors.

Gastrointestinal stromal tumors are known to occur at a similar incidence between races worldwide. It is known that gastrointestinal stromal tumors are relatively rare with an annual incidence of 10 to 20 per million population, and about 20-30% of all gastrointestinal stromal tumors show a clinically malignant course (Miettinen M, Lasota J. Gastrointestinal stromal tumors: definition, clinical, histological, immunohistochemical, and molecular genetic features and differential diagnosis. Virchows Arch 2001; 438:1-12). Considering that the population of Korea is about 50 million people, it is estimated that 500 to 1,000 new gastrointestinal stromal tumor patients will occur annually, and the number of patients with a malignant course will be about 100 to 300 people annually. Gastrointestinal stromal tumor occurs a little more in males than in females, and occurs most often in 55 to 65 years of age, but also occurs in 20 to 30 years of age and pediatric age.

Accordingly, the present inventors have conducted studies to develop a novel substance that may be used for the treatment of gastrointestinal stromal tumor, thereby completing the present invention.

DISCLOSURE

Technical Problem

An object of the present invention is to provide a pharmaceutical composition for preventing or treating gastrointestinal stromal tumor containing a compound represented by the following Formula 1 or a pharmaceutically acceptable salt thereof:

[Formula 1]

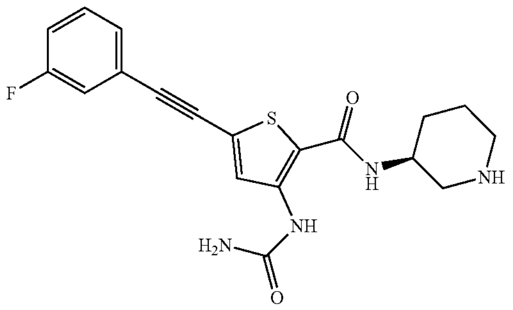

Another object of the present invention is to provide a food composition for preventing or ameliorating gastrointestinal stromal tumor containing a compound represented by the following Formula 1 or a pharmaceutically acceptable salt thereof:

[Formula 1]

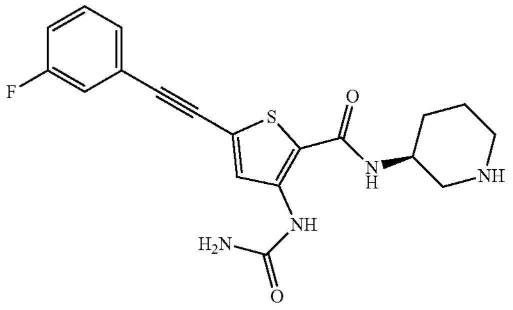

Still another object of the present invention is to provide a method for treating gastrointestinal stromal tumor comprising a step of administering, to a gastrointestinal stromal tumor patient, a pharmaceutical composition containing a compound represented by the following Formula 1 or a pharmaceutically acceptable salt thereof as an active ingredient:

[Formula 1]

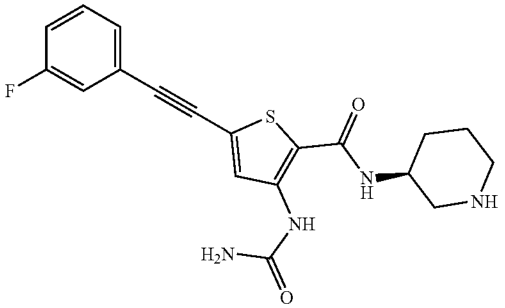

Yet another object of the present invention is to provide the use of a compound represented by the following Formula 1 or a pharmaceutically acceptable salt thereof for preventing or treating gastrointestinal stromal tumor:

[Formula 1]

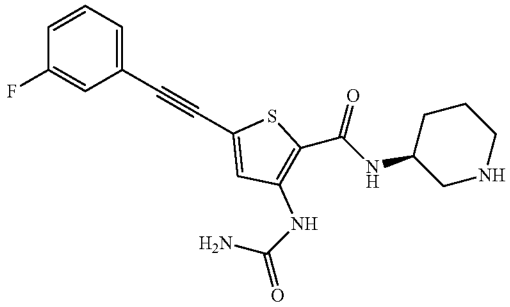

Technical Solution

One aspect of the present invention provides a pharmaceutical composition for preventing or treating gastrointestinal stromal tumor containing a compound represented by the following Formula 1 or a pharmaceutically acceptable salt thereof:

[Formula 1]

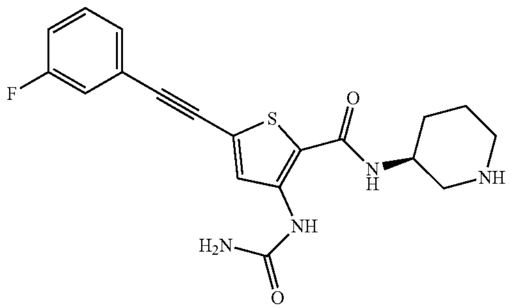

In one embodiment of the present invention, the gastrointestinal stromal tumor may be caused by substitution of valine for aspartic acid at amino acid position 816 of c-kit protein.

Another aspect of the present invention provides a food composition for preventing or ameliorating gastrointestinal stromal tumor containing a compound represented by the following Formula 1 or a pharmaceutically acceptable salt thereof:

[Formula 1]

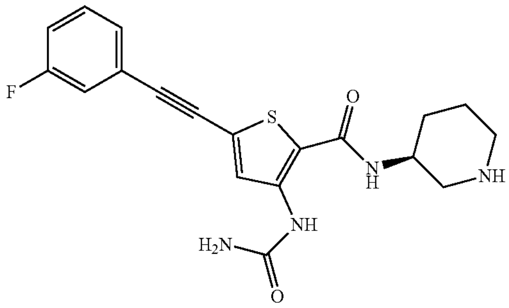

Still another aspect of the present invention provides a method for treating gastrointestinal stromal tumor comprising a step of administering, to a gastrointestinal stromal tumor patient, a pharmaceutical composition containing a compound represented by the following Formula 1 or a pharmaceutically acceptable salt thereof as an active ingredient:

[Formula 1]

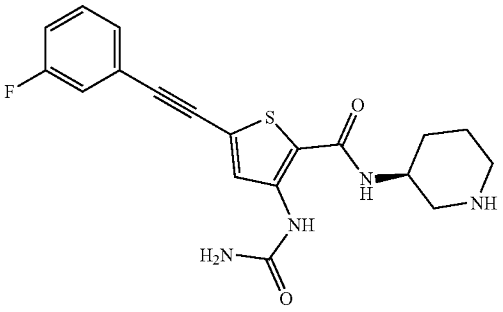

Yet another aspect of the present invention provides the use of a compound represented by the following Formula 1 or a pharmaceutically acceptable salt thereof for preventing or treating gastrointestinal stromal tumor:

[Formula 1]

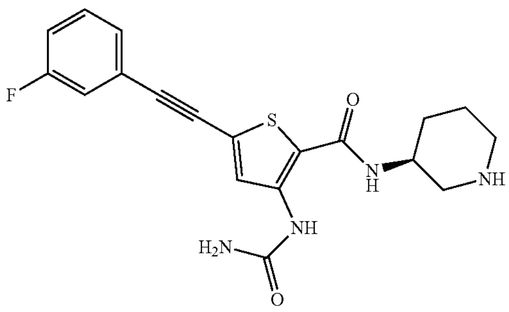

Still yet another aspect of the present invention provides the use of a compound represented by the following Formula 1 or a pharmaceutically acceptable salt thereof for preparing a pharmaceutical composition for preventing or treating gastrointestinal stromal tumor:

[Formula 1]

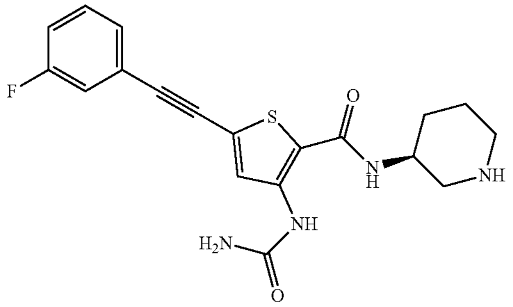

Advantageous Effects

The composition containing a 2,3,5-substituted thiophene compound according to one embodiment of the present invention has excellent inhibitory activity against gastrointestinal stromal tumor growth, and thus may be effectively used for the prevention, amelioration or treatment of gastrointestinal stromal tumor.

BEST MODE

Figure 1:
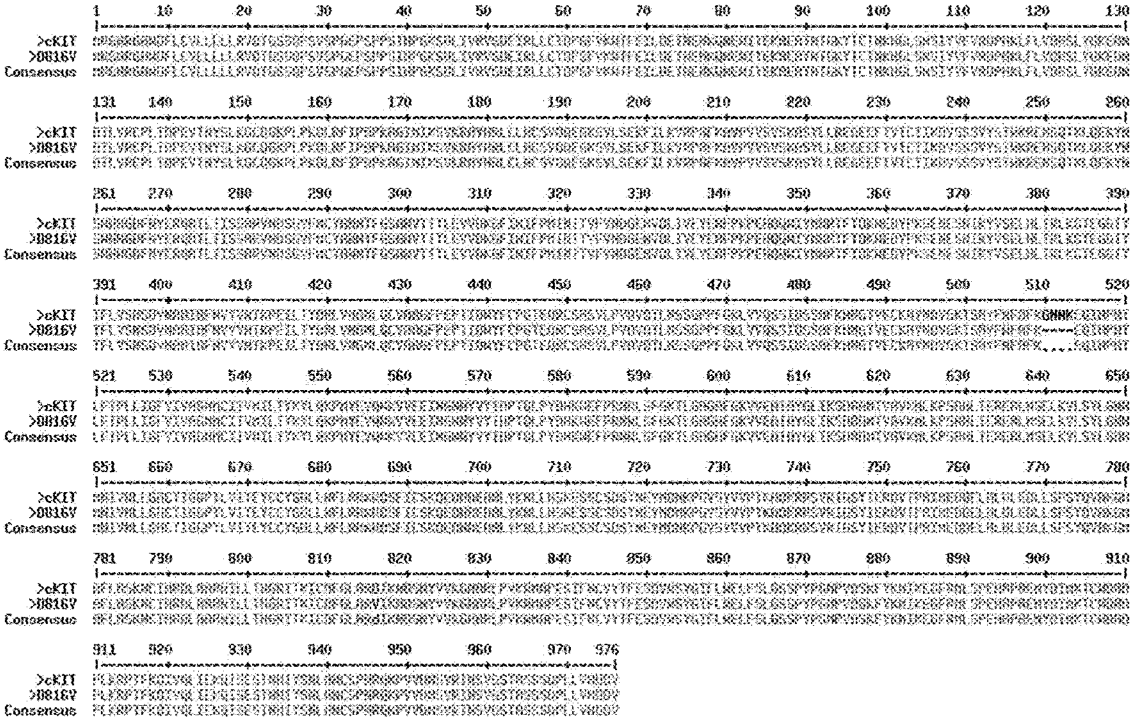
FIG. 1 shows a mutation of aspartic acid (D)-to-valine (V) substitution at amino acid position 816 in the amino acid sequence of c-kit protein.

One aspect of the present invention provides a pharmaceutical composition for preventing or treating gastrointestinal stromal tumor containing a compound represented by the following Formula 1 or a pharmaceutically acceptable salt thereof:

[Formula 1]

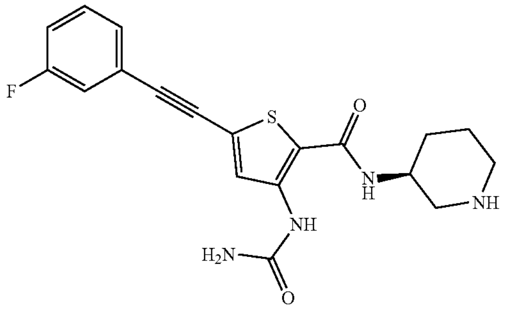

The compound represented by Formula 1, which is contained as an active ingredient in the pharmaceutical composition of the present invention, is (S)-5-((3-fluorophenyl)ethynyl)-N-(piperidin-3-yl)-3-ureidothiophene-2-carboxamide.

PHI-101, the compound represented by Formula 1 according to the present invention, inhibits the proliferation of the human GIST cell line GIST-T1. Since PHI-101 exhibits an $IC_{50}$ value of 36 nM in GIST-T1 cells, it may exhibit excellent inhibitory activity against gastrointestinal stromal tumor.

The pharmaceutical composition according to one embodiment of the present invention may be administered together with one or more anticancer agents.

For the treatment of gastrointestinal stromal tumor, the pharmaceutical composition according to one embodiment of the present invention may be used alone or in combination with surgery, hormone therapy, chemotherapy, radiotherapy and/or methods using biological response modifiers.

The pharmaceutical composition of the present invention may contain pharmaceutically acceptable carriers. The pharmaceutically acceptable carriers contained in the pharmaceutical composition of the present invention are those that are commonly used in the manufacture of medicaments, and examples thereof include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil. The pharmaceutical composition of the present invention may further contain, in addition to the above-described components, a lubricant, a wetting agent, a sweetening agent, a flavoring agent, an emulsifying agent, a suspending agent, a preservative, and the like. Suitable pharmaceutically acceptable carriers and formulations are described in detail in *Remington: the science and practice of pharmacy* $22^{nd}$ edition (2013).

The pharmaceutical composition of the present invention may contain various bases and/or additives necessary and appropriate for formulation, and may be prepared to further contain known components such as nonionic surfactants, silicone polymers, extender pigments, fragrances, preservatives, bactericides, oxidation stabilizers, organic solvents, ionic or nonionic thickeners, softeners, antioxidants, free radical scavengers, opacifiers, stabilizers, emollients, silicones, α-hydroxy acids, antifoaming agents, humectants, vitamins, insect repellents, fragrances, preservatives, surfactants, anti-inflammatory agents, substance P antagonists, fillers, polymers, propellants, basifying or acidifying agents, or coloring agents, within a range that does not impair the effect thereof.

A suitable dosage of the pharmaceutical composition of the present invention may be variously prescribed depending on factors such as formulation method, administration method, the patient's age, weight, sex, disease condition, and diet, the time of administration, the route of administration, excretion rate, and response sensitivity. The dosage of the pharmaceutical composition of the present invention may be 0.001 to 1,000 mg/kg for adults.

The pharmaceutical composition of the present invention may be administered orally or parenterally.

The pharmaceutical composition of the present invention may be administered orally in various dosage forms, for example in the form of tablets, pills, hard/soft capsules, solutions, suspensions, emulsions, syrups, granules, elixirs, troches, etc., and may further contain various excipients, for example, wetting agents, sweetening agents, aromatics, preservatives, and the like. Specifically, when the composition of the present invention is formulated in an oral dosage form, it may further contain appropriate carriers, excipients and diluents, which are commonly used in the preparation thereof. As the carrier, excipient and diluent, for example, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and/or mineral oil may be used, without being limited thereto. In addition, the composition may be prepared to contain diluents or excipients such as fillers, extenders, binders, wetting agents, disintegrants, surfactants, etc., which are commonly used in formulation, and it may further contain a lubricant such as magnesium stearate or talc, in addition to the excipients.

The pharmaceutical composition of the present invention may be administered parenterally, for example, by subcutaneous injection, intravenous injection or intramuscular injection, without being limited thereto.

For the preparation of a parenteral dosage form, for example, the pharmaceutical composition of the present invention may be mixed with a stabilizer or buffer in a water to obtain a solution or suspension, which may be then prepared in an ampoule or vial unit dosage form. In addition, the composition may be sterilized, or may further contain an adjuvant, such as a preservative, a stabilizer, a hydrating agent or an emulsification accelerator, a salt for controlling osmotic pressure, or a buffer, and other therapeutically beneficial substances, and may be formulated according to a conventional method.

According to one embodiment of the present invention, the gastrointestinal stromal tumor may be caused by substitution of valine for aspartic acid at amino acid position 816 of c-kit protein.

85 to 90% of gastrointestinal stromal tumors are caused by mutations in the KIT or PDGFRα gene, of which mutations in the KIT gene are the most common with a frequency of 75 to 80%. The compound represented by Formula 1 has excellent inhibitory activity against gastrointestinal stromal tumors having a mutation of aspartic acid, specifically, a mutation of aspartic acid-to-valine substitution, at amino acid position 816 of c-kit protein, and thus may be effectively used for the prevention or treatment of gastrointestinal stromal tumors having this mutation.

Still another aspect of the present invention provides a method for treating gastrointestinal stromal tumor comprising a step of administering, to a gastrointestinal stromal tumor patient, a pharmaceutical composition containing the compound represented by the following Formula 1 or pharmaceutically acceptable salt thereof as an active ingredient.

The pharmaceutical composition according to one embodiment of the present invention contains the compound represented by Formula 1 as an active ingredient, and in particular, exhibits an excellent anticancer effect against a gastrointestinal stromal tumor having a mutation of aspartic acid at amino acid position 816 of c-kit protein. Thus, the method may further comprise, before administering the pharmaceutical composition of the present invention, a companion diagnosis step of selecting a group of patients on whom the compound represented by Formula 1 exhibits effects, and the companion diagnosis step may be performed by a gastrointestinal stromal tumor diagnostic method known in the art.

As used herein, the term "companion diagnosis" refers to a diagnosis for predicting patient's responsiveness to a specific drug therapy.

Yet another aspect of the present invention provides a food composition for preventing or ameliorating gastrointestinal stromal tumor containing a compound represented by the following Formula 1 or a pharmaceutically acceptable salt thereof:

[Formula 1]

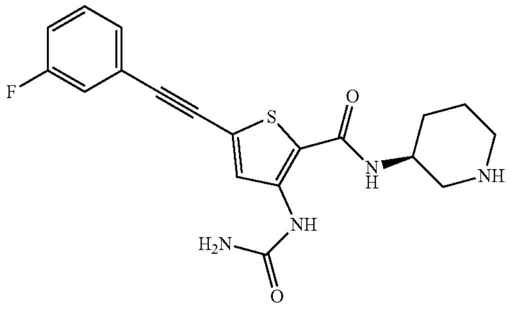

The food composition of the present invention may be prepared by adding raw materials and ingredients, which are commonly added in the art. In addition, the food composition may contain, as additional ingredients, various flavorings or natural carbohydrates, like conventional food compositions, in addition to containing the compound represented by Formula 1 as an active ingredient.

According to one embodiment of the present invention, the natural carbohydrates may be conventional sugars, such as monosaccharides (e.g., glucose, fructose, etc.), disaccharides (e.g., maltose, sucrose, etc.), and polysaccharides (e.g., dextrin, cyclodextrin, etc.), and sugar alcohols such as xylitol, sorbitol, or erythritol. The flavorings may include natural flavorings (thaumatin), stevia extracts (e.g., rebaudioside A, glycyrrhizin, etc.) and/or synthetic flavorings (saccharin, aspartame, etc.).

The food composition of the present invention may be formulated as a food composition further containing one or more food-acceptable or pharmaceutically acceptable carriers in addition to the above-described active ingredient. The food composition may be formulated in the form of tablet, capsule, powder, granule, liquid, pill, solution, syrup, juice, suspension, emulsion, or drop. For example, for formulation in the form of tablet or capsule, the active ingredient may be combined with an oral, non-toxic pharmaceutically acceptable inert carrier such as ethanol, glycerol, or water.

The food composition of the present invention may contain a vitamin mixture consisting of vitamin A acetate, vitamin E, vitamin B1, vitamin B2, vitamin B6, vitamin B12, vitamin C, biotin, nicotinic acid amide, folic acid, and calcium pantothenate, and one or more minerals such as ferrous sulfate, zinc oxide, magnesium carbonate, potassium phosphate monobasic, potassium phosphate dibasic, potassium citrate, calcium carbonate, and magnesium chloride, which may be commonly added in the art.

If necessary, a suitable binder, lubricant, disintegrant and coloring agent may also be contained as a mixture. Examples of suitable binders include natural sugars such as starch, gelatin, glucose or beta-lactose, natural and synthetic gums such as corn sweeteners, acacia, tragacanth or sodium oleate, sodium stearate, magnesium stearate, sodium benzoate, sodium acetate, sodium chloride, and the like. Examples of the disintegrants include starch, methyl cellulose, agar, bentonite, xanthan gum, and the like.

These components may be used independently or in combination, and the proportion of these additives may be selected within a range of from 0 to about 20 parts by weight based on 100 parts by weight of the food composition of the present invention, without being limited thereto.

Meanwhile, it is possible to prepare a variety of foods by applying methods for preparing various formulations, known to those skilled in the art, to the food composition of the present invention. For example, the food composition of the present invention may be prepared as a common health functional food formulation such as a beverage, a pill, or a powder, without being limited thereto.

The food composition of the present invention has a particularly excellent ability to inhibit the growth of gastrointestinal stromal tumor cell lines, and thus may be effectively used for the prevention or amelioration of gastrointestinal stromal tumor.

Still yet another aspect of the present invention provides a method for treating gastrointestinal stromal tumor comprising a step of administering, to a gastrointestinal stromal tumor patient, a pharmaceutical composition containing a compound represented by the following Formula 1 or a pharmaceutically acceptable salt thereof as an active ingredient:

[Formula 1]

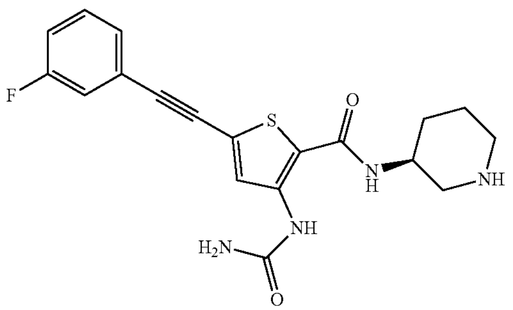

A further aspect of the present invention provides the use of a compound represented by the following Formula 1 or a pharmaceutically acceptable salt thereof for preventing or treating gastrointestinal stromal tumor:

[Formula 1]

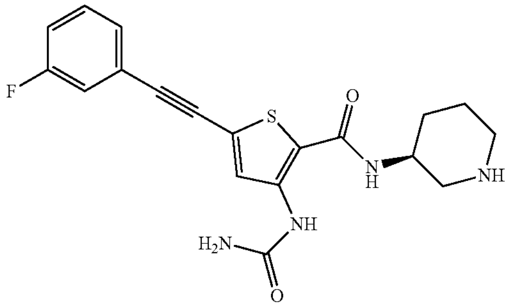

Another further aspect of the present invention provides the use of a compound represented by the following Formula 1 or a pharmaceutically acceptable salt thereof for preparing a pharmaceutical composition for preventing or treating gastrointestinal stromal tumor:

[Formula 1]

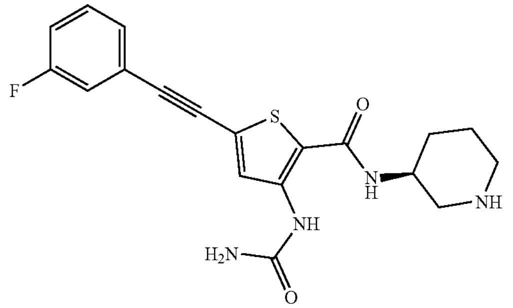

MODE FOR INVENTION

Hereinafter, the present invention will be described in detail with reference to one or more examples. However, these examples are for illustrating the present invention, and the scope of the present disclosure is not limited by these examples.

Example 1. Evaluation of Inhibitory Activity of PHI-101 Against c-Kit Mutant Cell Line 1-1. Evaluation of Inhibitory Activity Against Growth of c-Kit Mutant Cell Line The inhibitory activity of the compound represented by Formula 1 (hereinafter referred to as "PHI-101") against a c-kit mutant cell line was measured.

[Formula 1]

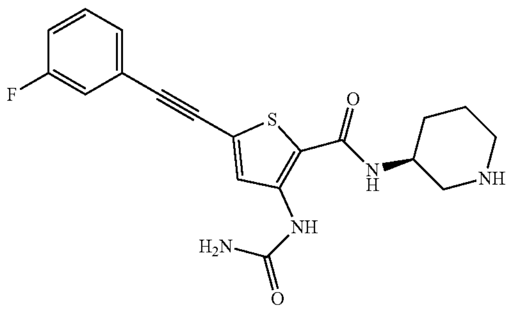

Specifically, 100 μl of a Ba/F3 cell line with a c-kit D816V mutation (FIG. 1) was added to each well of a 96-well plate at a concentration of 10,000 cells/100 μl. After 4 hours, 100 μl of the Ba/F3 cell line was treated with 0.5 μl of each of control compounds and PHI-101 (10-point 1:3 serial dilutions) to a final concentration of up to 50 μM, and cultured at 37° C. under 5% $CO_2$ for 72 hours. As the control compounds, imatinib and sunitinib which are c-kit inhibitors were used. After culture, the cells were counted using a Celltiter glo assay kit (Promega), and the 50% growth inhibition values ($GI_{50}$, μM) of the control compounds and PHI-101 were measured.

As a result, it was confirmed that PHI-101 exhibited higher inhibitory activity against the c-kit D816V Ba/F3 mutant cell line than the control compounds, and exhibited higher selectivity for the c-kit D816V Ba/F3 mutant cell line than for the parental Ba/F3 cell line (Table 1).

TABLE 1

| | $GI_{50}$ (μM) | | |
|---|---|---|---|
| | PHI-101 | Imatinib | Sunitinib |
| cKIT D816V Ba/F3 | 0.912 | 11.48 | 2.647 |
| Parental Ba/F3 | 5.010 | 12.73 | 13.32 |

1-2. Evaluation of Inhibitory Activity Against c-Kit Phosphorylation and Downstream Signaling The inhibitory activities of the control compound and PHI-101 against c-kit phosphorylation and downstream signaling (p-STAT3, p-ERK1/2) in the c-kit D816V mutant Ba/F3 cell line were measured, and as control compounds, sunitinib and dasatinib were used.

Specifically, the c-kit D816V mutant Ba/F3 cell line was dispensed at a density of $1\times10^6$ cells/ml, treated with each of the control compounds and PHI-101 at concentrations of 0.1, 1 and 10 μM, and then cultured for 2 hours. Lysates of the cells were obtained using lysis buffer (50 mM Tris-HCl pH7.5, 1% NP40, 1 mM EDTA, 150 mM NaCl, 5 mM, $Na_3VO_4$ and 2.5 mM NaF, and a protease inhibitor cocktail). Equal amounts of the cell lysates were electrophoresed using 8% SDS-PAGE gel at 100 V for 1 hour and 30 minutes, and the separated protein was electrically transferred to nitrocellulose membranes. The membranes were blocked with 5% skim milk at room temperature for 30 minutes, and allowed to react with primary antibodies (diluted 1:5,000), including p-c-kit tyrosine 719 (Y719), p-STAT3 tyrosine 705 (Y705) and p-ERK1/2 threonine 202/tyrosine 204 (T202/Y204) at 4° C. for 16 to 20 hours. As a control for comparing the level of expression, anti-β actin (diluted at a ratio of 1:10,000) was used as a primary antibody. Thereafter, the membranes were washed 3 times with TBST (Tris-buffered saline, 0.1% Tween 20) for 5 minutes each time, and then incubated with an HRP-conjugated anti-rabbit secondary antibody (diluted at a ratio of 1:10,000) at room temperature for 1 hour. Next, the membranes were washed three times with TBST for 5 minutes each time and treated with a chemiluminescent substrate reagent, and the expression level of the protein was measured by detecting luminescence with an X-ray film in the dark.

Figure 2:
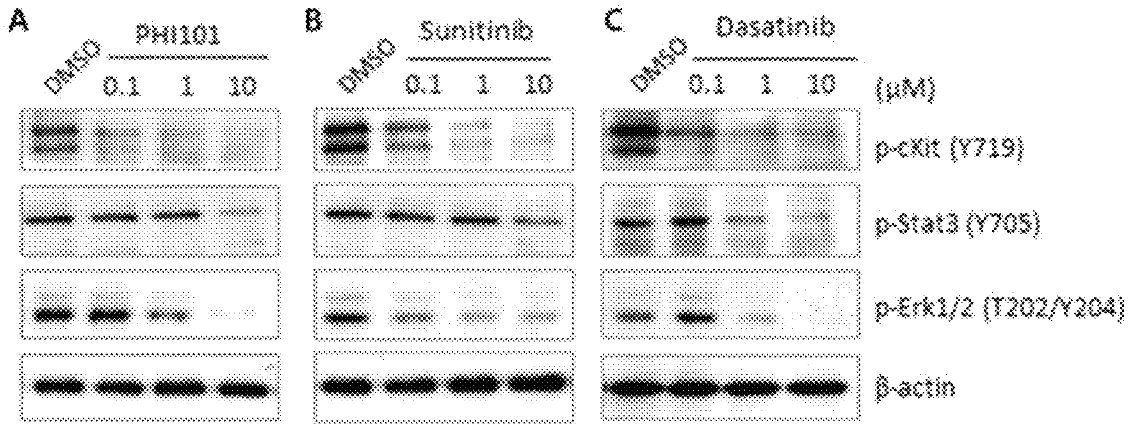
FIG. 2 shows the inhibitory activities of PHI-101 (A) according to an embodiment of the present invention, sunitinib (B) and dasatinib (C) against signaling in the c-kit D816V Ba/F3 cell line at various treatment concentrations.

As a result, it was confirmed that PHI-101 showed higher inhibitory activity against p-c-kit (Y719) phosphorylation than the control compounds, and showed downstream signaling (p-STAT3, p-ERK1/2) inhibitory activity similar to those of the control compounds (FIG. 2).

1-3. Evaluation of Apoptotic Effect

The c-kit D816V mutant Ba/F3 cell line was treated with PHI-101, and then the apoptotic effect of PHI-101 was analyzed.

Specifically, the c-kit D816V mutant Ba/F3 cell line was adjusted to a concentration of $1\times10^6$ cells/ml and treated with each of PHI-101 at concentrations of 0.1, 1 and 10 μM and the control compound sunitinib at concentrations of 1 and 10 μM for 24 hours. Thereafter, the medium was removed and the cells were washed once with 1 ml PBS. The PBS was removed by centrifugation at 1,000 rpm for 5 minutes. The cells were dissolved in 100 μl of PBS containing $Ca^{2+}$ and $Mg^{2+}$ and allowed to react with 5 μl of Annexin V for 20 minutes. After completion of the reaction, 400 μl of PBS containing $Ca^{2+}$ and $Mg^{2+}$ was added, and 5 μl of propidium iodide (PI) was added, and then the degree of apoptotic cell death was analyzed by FACS (fluorescence activated cell sorter) assay using a flow cytometer (FACS-C6, BD).

Figure 3:
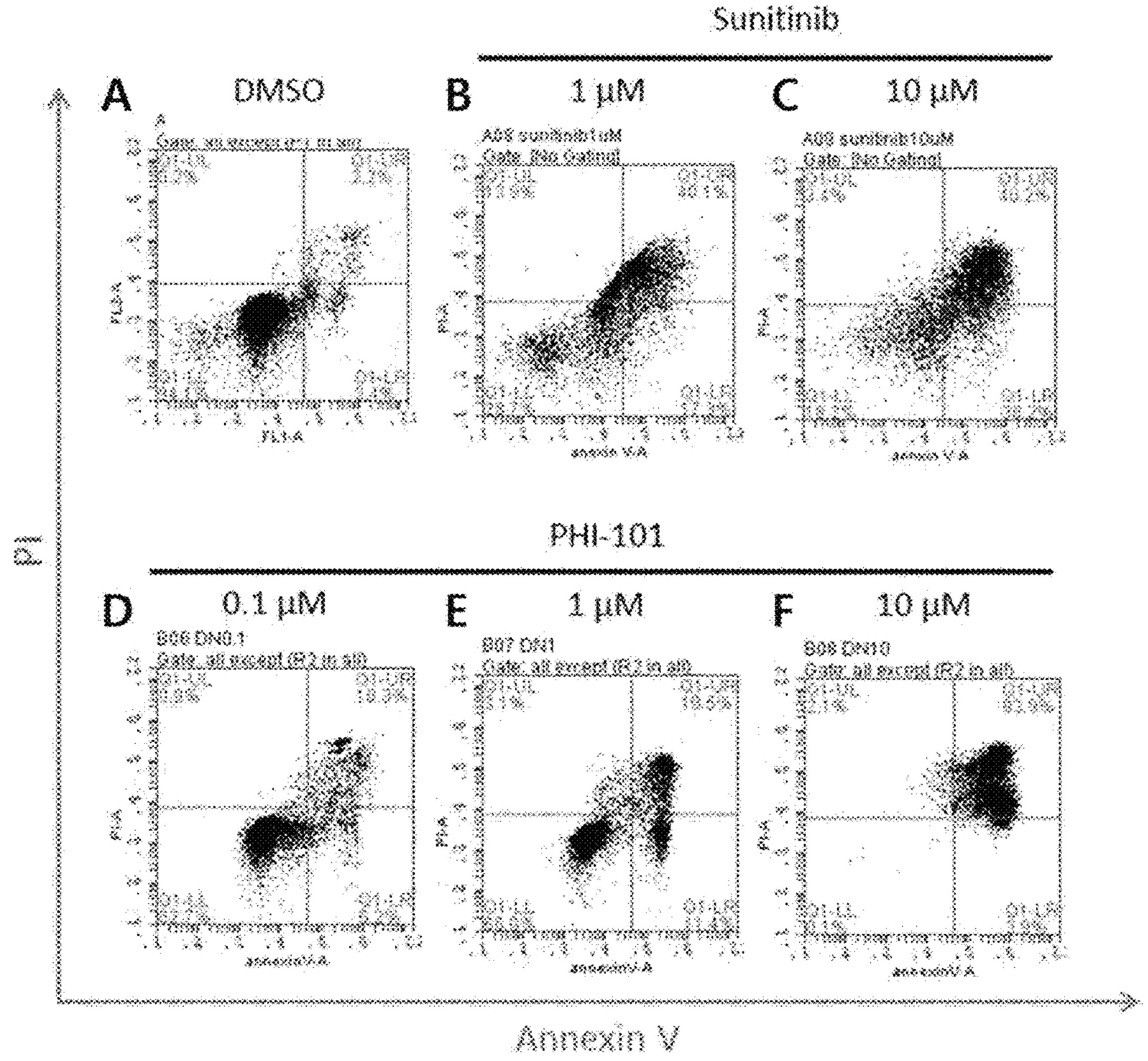
FIG. 3 depicts graphs showing the results of Annexin V-PI FACS analysis of the c-kit D816V Ba/F3 cell line treated with various concentrations of dimethyl sulfoxide (DMSO) (A) as a negative control, sunitinib (B) and (C), and PHI-101 (D), (E) and (F) according to one embodiment of the present invention.

As a result, it was confirmed that PHI-101 strongly induced apoptosis even at a concentration of 0.1 μM, and apoptosis increased in a concentration-dependent manner (FIG. 3).

1-4. Evaluation of Inhibitory Effect Against Cell Cycle Progression

The c-kit D816V mutant Ba/F3 cell line was treated with 1 μM of PHI-101, and then the SubG1/GO-1 population was analyzed by cell cycle FACS assay.

Specifically, the c-kit D816V mutant Ba/F3 cell line was adjusted to a concentration of $1\times10^6$ cells/ml and treated with each of PHI-101 and the control compound sunitinib at a concentration of 1 μM for 24 hours. Thereafter, the medium was removed, and the c-kit D816V mutant Ba/F3 cell line was fixed in 70% ethanol at 4° C. for 24 hours, and then incubated in a PBS buffer solution containing 40 μg/ml of propidium iodide (PI) and 100 μg/ml of RNase for 30 minutes to completely stain the total DNA. Cell cycle analysis of the stained cells was performed using a flow cytometer (FACS-C6, BD). The proportion of cells in G0/G1 phase, S phase and G2/M phase was measured, and based on the measurement results, the SubG1/GO-1 population was determined.

Figure 4:
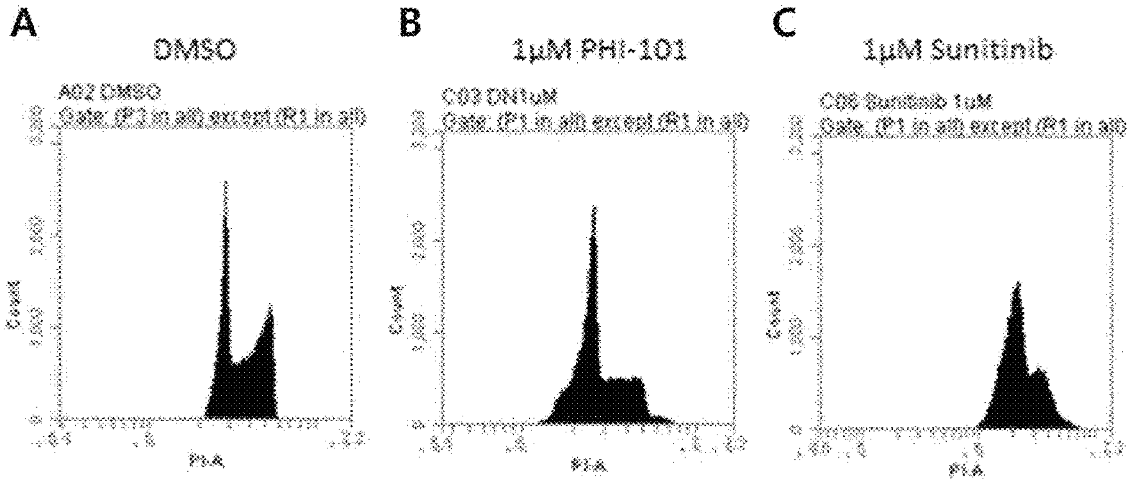
FIG. 4 depicts graphs showing the results of cell cycle FACS analysis of the c-kit D816V Ba/F3 cell line treated with dimethyl sulfoxide (DMSO) (A) as a negative control, sunitinib (B), and PHI-101 (C) according to one embodiment of the present invention.
Figure 5:
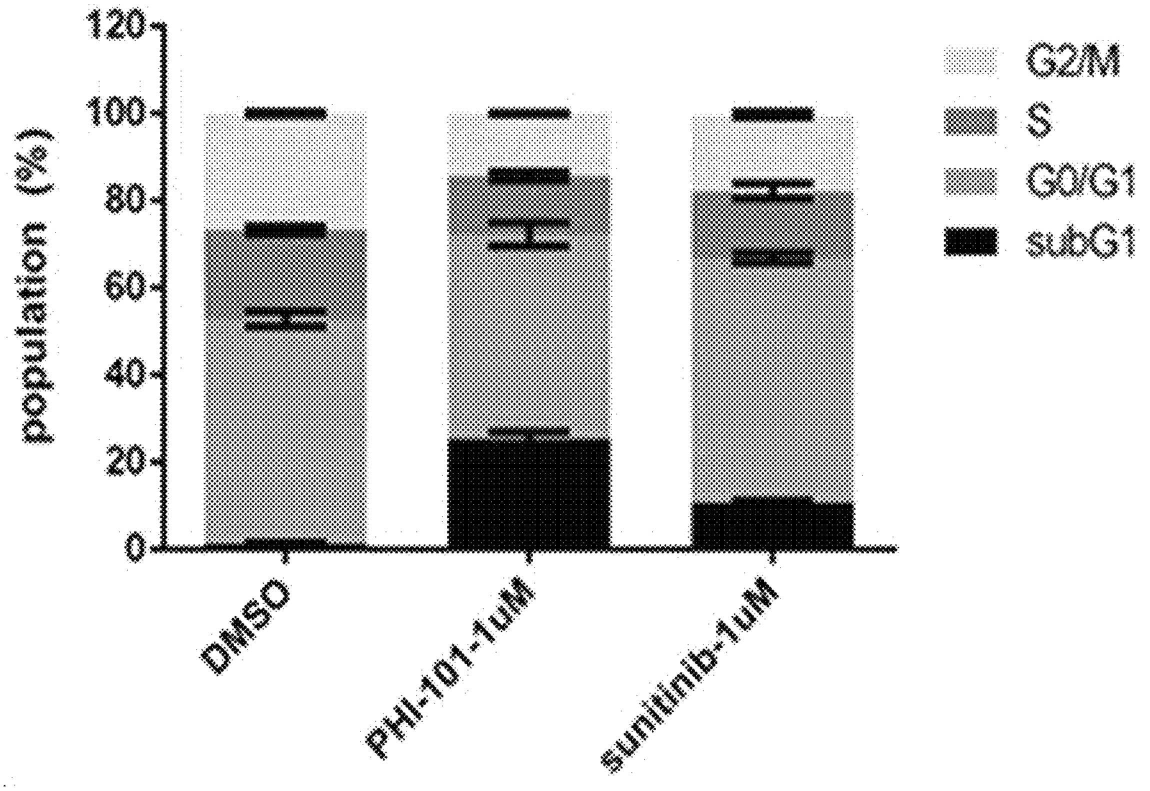
FIG. 5 is a graph showing the population at each cell cycle phase of the c-kit D816V Ba/F3 cell line treated with dimethyl sulfoxide (DMSO) (A) as a negative control, sunitinib (B), and PHI-101 (C) according to one embodiment of the present invention.

As a result, it was confirmed that the SubG1/GO-1 population was increased by treatment with PHI-101, and thus the cell cycle progression of the c-kit D816V mutant Ba/F3 cell line was inhibited (FIGS. 4 and 5).

Example 2. Evaluation of Inhibitory Activity of PHI-101 Against Gastrointestinal Stromal Tumor Cell Line

2-1. Measurement of Inhibitory Activity Against Growth of Gastrointestinal Stromal Tumor Cell Line The inhibitory activity of PHI-101 against a gastrointestinal stromal tumor (GIST) cell line was measured.

Specifically, 100 μl of the GIST-T1 cell line was added to each well of a 96-well plate at a concentration of 5,000 cells/100 μl. After 24 hours of stabilization, 100 μl of the GIST-T1 cell line was treated with 0.5 μl of each of control compounds and PHI-101 (⅓ serial dilution, 10 points) to a final concentration of up to 50 μM, and cultured at 37° C. under 5% $CO_2$ for 72 hours. As the control compounds, imatinib, dasatinib, sunitinib and ponatinib, which are c-kit inhibitors, were used. After culture, the cells were counted using a Celltiter glo assay kit (Promega), and the 50% growth inhibition values ($GI_{50}$, μM) of the control compounds and PHI-101 were measured.

As a result, it was confirmed that PHI-101 exhibited GIST-T1 cell line inhibitory activity similar to those of the control compounds (Table 2).

TABLE 2

| | $GI_{50}$ (μM) | | | | |
|---|---|---|---|---|---|
| | PHI-101 | Imatinib | Dasatinib | Sunitinib | Ponatinib |
| GIST-T1 | 0.036 | 0.064 | 0.073 | 0.026 | — |

2-2. Evaluation of Inhibitory Activity Against c-Kit Phosphorylation and Downstream Signaling The inhibitory activities of control compounds and PHI-101 against c-kit phosphorylation and downstream signaling (p-AKT, p-ERK1/2, p-S6) in a gastrointestinal stromal tumor cell line were measured, and as the control compounds, imatinib and sunitinib were used.

Specifically, inhibitory activities against c-kit phosphorylation and downstream signaling were measured in the same manner as in Example 1-2, except that the GIST-T1 cell line was treated with each of control compounds at a concentration of 1 μM and PHI-101 at concentrations of 0.01, 0.1 and 1 μM, and p-c-kit tyrosine 703 (Y703), p-AKT threonine 308 (T308), p-AKT serine 473 (S473) tyrosine 705 (Y705), p-ERK1/2 and p-S6 serine 235/serine 236 (S235/S236), each diluted at 1:3000, were used as primary antibodies.

Figure 6:
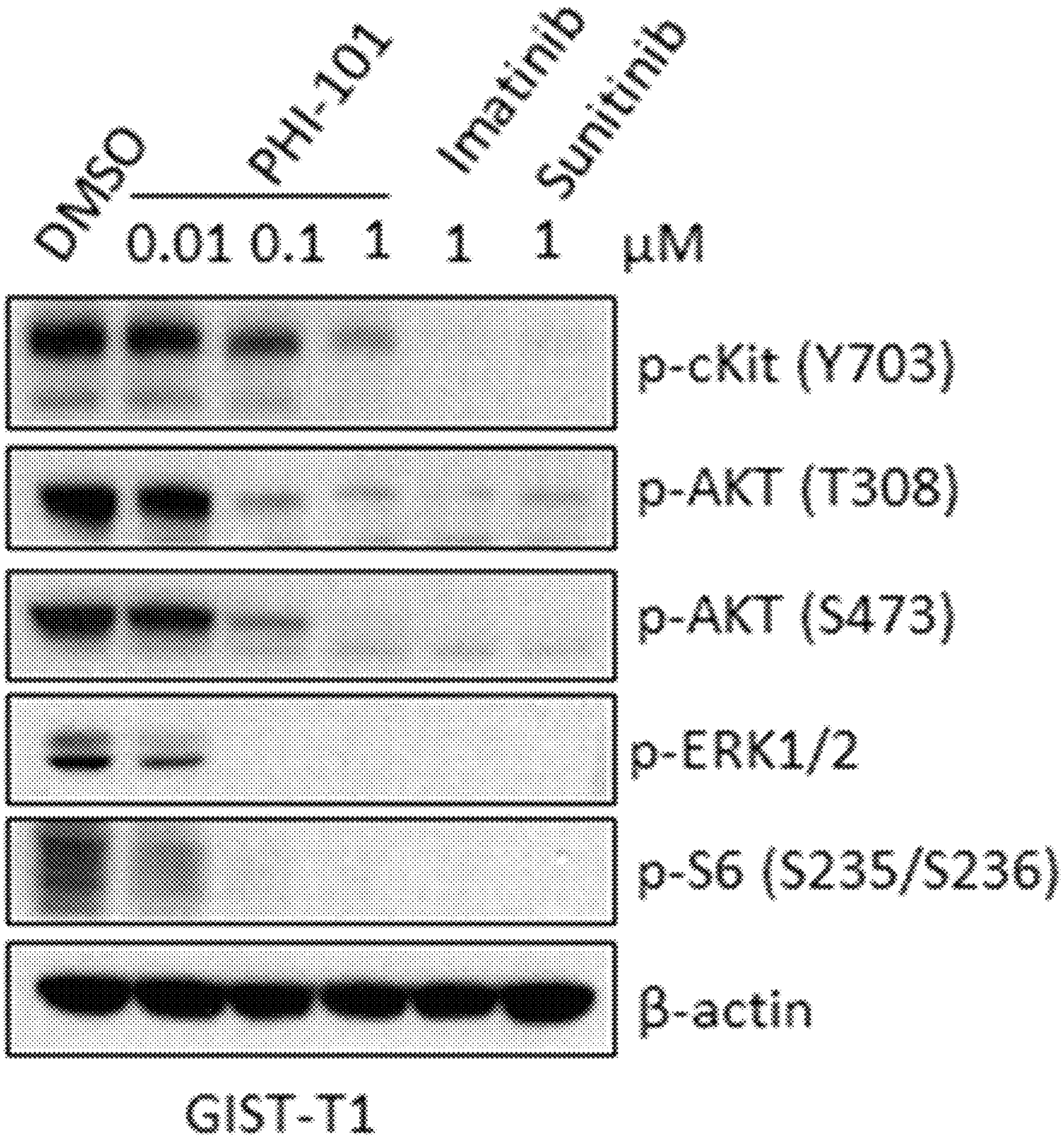
FIG. 6 shows the inhibitory activities of PHI-101 according to one embodiment of the present invention, imatinib and sunitinib against signaling in the GIST-T1 cell line at various treatment concentrations.

As a result, it was confirmed that PHI-101 decreased c-kit phosphorylation and downstream signaling in a concentration-dependent manner, and exhibited downstream signaling inhibitory activity similar to those of the control compounds (FIG. 6).

2-3. Evaluation of Apoptotic Effect

A gastrointestinal stromal tumor cell line was treated with PHI-101, and the level of cleaved PARP, an apoptosis marker, was analyzed. As control compounds, imatinib and sunitinib were used.

Specifically, the apoptotic effect of PHI-101 against the GIST-T1 cell line was analyzed in the same manner as in Example 1-2, except that the GIST-T1 cell line was treated with each of the control compounds at a concentration of 1 μM and PHI-101 at concentrations of 0.01, 0.1 and 1 μM for 24 hours, and that cleaved PARP diluted at 1:3,000 was used as a primary antibody.

Figure 7:
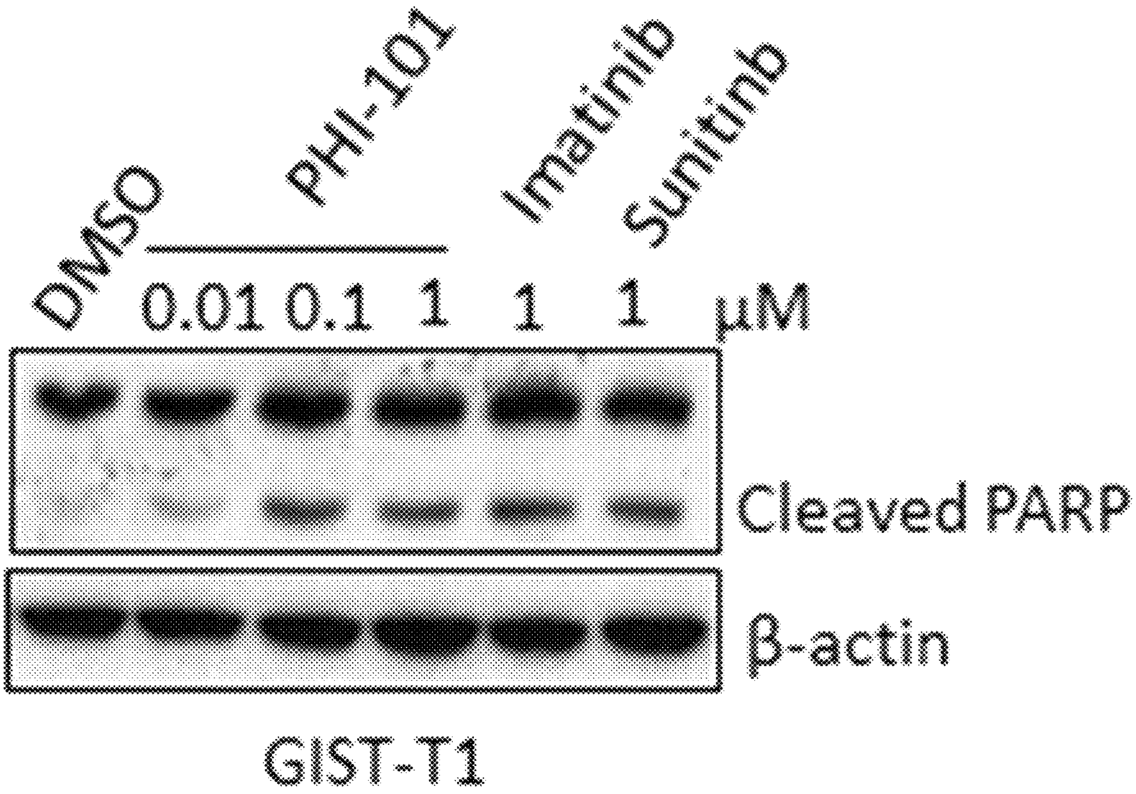
FIG. 7 is a photograph showing the results of Western blot analysis performed to examine the apoptotic effects of PHI-101 according to one embodiment of the present invention, imatinib and sunitinib against the GIST-T1 cell line at various treatment concentrations.

As a result, it was confirmed that the level of cleaved PARP increased in a manner dependent on the concentration of PHI-101 in the GIST-T1 cell line, indicating that PHI-101 has an apoptotic effect against the gastrointestinal stromal tumor cell line (FIG. 7).

Example 3. Evaluation of Effect of PHI-101 on Prolongation of Survival Time of c-Kit D816V Ba/F3 Cell Line Xenograft Mouse Model

3-1. Establishment of c-Kit D816V Ba/F3 Cell Line Xenograft Mouse Model

As mice, 6-8-week-old NOD SCID female mice (18 to 22 g) (GemPharmatech Co., Ltd.) were prepared. Mice were acclimatized for 7 days before use in the experiment, and mice with abnormal health were excluded from the experiment. Mice were bred in a cage (300×180×150 mm) at a 22±3° C. and a relative humidity of 40% to 70% with a 12-hr light/12-hr dark cycle. Mice were allowed access to sterilized dry granular food (Beijing Keaoxieli Feed Co., Ltd., Beijing, China) and water ad libitum for the entire experimental period except for the period specified in the protocol.

50 ml of c-kit D816V mutant Ba/F3 cells suspension cultured in a 75 T flask were placed in a conical tube and centrifuged at 800 rpm for 2 minutes, centrifuged with DPBS (Dulbecco's Phosphate-Buffered Saline, Welgene) at 800 rpm for 2 minutes, washed, and then suspended in RPMI1640 (Welgene) without antibiotics and fetal bovine serum (FBS). Thereafter, the cells were stained with trypan blue and counted with a hemocytometer. The cells were adjusted to a concentration of $1\times10^7$ viable cells/ml, and 100 μl of the cells were dispensed in an insulin syringe. Mice were immobilized using a restrainer, and then the cells were administered intravenously into the tail veins, thereby constructing a c-kit D816V Ba/F3 cell line xenograft mouse model.

3 days after transplantation of the c-kit D816V mutant Ba/F3 cell line, 6 mice were assigned to each group, and each of imatinib at a dose of 90 mg/kg, sunitinib at doses of 20 and 40 mg/kg and PHI-101 at doses of 7, 20, 40, and 80 mg/kg was orally administered daily to the mice until the mice died. For oral administration, each compound was dissolved in 5% 1-methyl-2-pyrrolidone and then completely mixed in 15% Kolliphor, 30% PEG E400 HS15 and 50% 0.05M citric acid.

3-2. Examination of Prolongation of Survival Time of Mice

In the c-kit D816V Ba/F3 cell line xenograft mouse model, whether the survival time of the mice was prolonged by administration of PHI-101 was examined.

Specifically, while the presence or absence of abnormalities in the mouse model of Example 3-1 was monitored daily by checking the skin condition, bleeding and stool status, whether the body weight changed was checked by measuring the mouse weight at intervals of 3 days after the start of oral administration of each drug. In addition, while the oral administration was performed daily, whether the mice dead was recorded by checking the state of the mice. For each data, one-way ANOVA was used to test the significance of each group, and for the lifespan time of the mice, a graph was plotted using Kaplan Meier survival analysis, and the median survival time was calculated.

Figure 8:
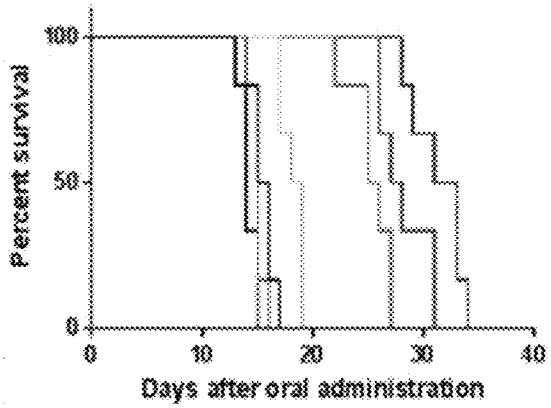
FIG. 8 depicts a graph and table showing the effects of oral administration of PHI-101 according to one embodiment of the present invention, imatinib and sunitinib on the prolongation of the survival time of a c-kit D816V Ba/F3 cell line xenograft mouse model.

As a result, it was confirmed that, unlike the control compounds having no effect on the prolongation of the survival time, PHI-101 had an effect of prolonging the survival time by 3 days compared to the vehicle-administered group even at a low dose of 7 mg/kg, and the survival time of the group to which PHI-101 was administered at a dose of 80 mg/kg was doubled compared to that of the vehicle-administered group (FIG. 8).

So far, the present invention has been described with reference to the embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention.

The invention claimed is:
m

1. A method for treating gastrointestinal stromal tumor caused by substitution of valine for aspartic acid at amino acid position 816 of c-kit protein, comprising the step of administering, to a gastrointestinal stromal tumor patient, a pharmaceutical composition containing a compound represented by the following Formula 1 or a pharmaceutically acceptable salt thereof as an active ingredient:

[Formula 1]

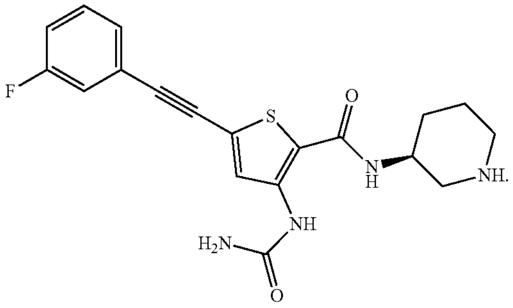

2. A method for treating gastrointestinal stromal tumor caused by substitution of valine for aspartic acid at amino acid position 816 of c-kit protein, comprising the step of administering, to a gastrointestinal stromal tumor patient, a compound represented by the following Formula 1 or a pharmaceutically acceptable salt thereof:

[Formula 1]

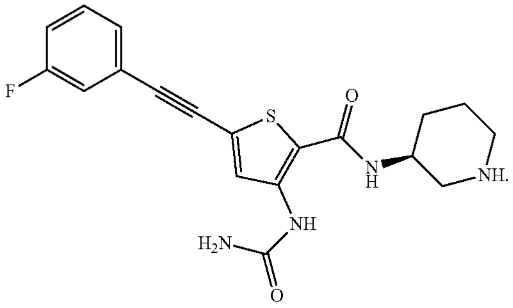

* * * * *